United States Patent [19]

Ensing, deceased

[11] 4,178,384

[45] Dec. 11, 1979

[54] PYRETHROID INSECT REPELLENT

[75] Inventor: Kenneth J. Ensing, deceased, late of Middleport, N.Y., by Lois K. Ensing, executrix

[73] Assignee: FMC Corporation, Philadelphia, Pa.

[21] Appl. No.: 758,981

[22] Filed: Jan. 13, 1977

Related U.S. Application Data

[63] Continuation-in-part of Ser. No. 669,371, Mar. 22, 1976, abandoned.

[51] Int. Cl.$^2$ .............................................. A01N 9/24
[52] U.S. Cl. ............................ 424/305; 424/DIG. 10
[58] Field of Search ............... 424/305, 306, DIG. 10

[56] References Cited

U.S. PATENT DOCUMENTS 4,020,181  4/1977  Blackman et al. .................. 424/305

FOREIGN PATENT DOCUMENTS

73/3528  5/1973  South Africa .

OTHER PUBLICATIONS

Elliott et al., "Nature," vol. 246 (1973), pp. 169–170.
U.S. Dept. of Ag., "Secondary Testing Proc. for Animal Protectant Sprays," Livestock Insects Investigations, Kerryville, Texas, Feb. 28, 1972.
Burden, "Pest Control," vol. 43 (1975), p. 16.

*Primary Examiner*—V. D. Turner
*Attorney, Agent, or Firm*—Richard L. Hansen; Henry R. Ertelt

[57] ABSTRACT

The pyrethroid insecticide, 3-phenoxybenzyl 3-($\beta,\beta$-dichlorovinyl)-2,2-dimethylcyclopropanecarboxylate, is a potent repellent for a variety of insect pests, including acarids. This pyrethroid provides long-lasting protection when incorporated as the active component in repellent compositions and applied to areas from which it is desired to exclude such insect pests. The repellency extends to a broad range of species, including cockroaches, true bugs, flies, mites, aphids, and beetles, as well as mature and immature moths and butterflies.

6 Claims, No Drawings

PYRETHROID INSECT REPELLENT

REFERENCE TO PRIOR APPLICATION

This is a Continuation-in-Part of application Ser. No. 669,371, filed Mar. 22, 1976, now abandoned.

BACKGROUND OF THE INVENTION

1. Field of the Invention

This invention relates to the general field of chemical agents which control insects pests, especially repellent agents which discourage the presence of such pests, rather than insecticidal agents which kill them.

2. Description of the Prior Art

In many instances it is more advantageous to repel insect pests from a given place than it is to kill them after they have entered it. Some insect pests inherently are difficult to kill, or the nature of the place where the pests are found may make it undesirable to kill them there. It is considered to be more desirable to repel pests such as cockroaches and flies from the vicinity of food, food handling equipment and places where food is eaten, since contacts between food and transitory insects serve to spread disease. In a number of instances, such as in the treatment of growing crops, it is desirable to use repellents to prevent the movement of insect pests into an area and from one area to another. Foliage-feeding insect pests may be killed by applying an insecticide to the leaves upon which they feed, but death of the pests after they have fed on the foliage is less than satisfactory in the case of many crops; for example, the market value of tobacco and cabbage is decreased markedly by holes in the leaves caused by foliage-feeding insects.

Of course, if the repellent treatment must be renewed too often, requiring time-consuming reapplication of an expensive chemical, the fundamental advantages of repelling rather than killing the insects are outweighed by economic considerations. Thus, insect repellents with long residual activity are especially desired.

Over the years a number of different oils, greases, ointments and powders have been employed as insect repellents with varying degrees of success. Oil of citronella was reported to be an effective insect repellent as early as 1901. Another natural product, nicotine from tobacco, was used as a repellent as long ago as 1760. Since World War II, a number of synthetic insect repellents have been introduced. These include 2-hydroxyethyl octyl sulfide (U.S. Pat. No. 2,863,799), used principally as a cockroach repellent; organic diols (U.S. Pat. No. 2,407,205); N,N-diethylbenzamides (U.S. Pat. No. 2,408,389); esters of pyridine dicarboxylic acids (U.S. Pat. No. 2,757,120); amido detergent alkylates (U.S. Pat. No. 3,234,081); and 3,3-dibutyl-2-(2,2,4-trimethylpentyl) pseudourea acetate (U.S. Pat. No. 3,266,978). None of these is noted for especially long residual activity.

Pyrethrins, which are cyclopropanecarboxylates, the naturally occurring extracts from the blossoms of pyrethrum flowers (*Chrysanthemum cinerariae-folium*) grown mainly in East Africa, were widely used as insecticides before the advent of synthetic materials such as DDT. The pyrethrins are effective in killing a wide range of insect species, and they also function as insect repellents [Burden, *Pest Control*, 43, 16 (1975)], but they are short-lived. Although they display relatively low toxicity toward mammals and do not leave harmful residues, they undergo rapid biodegradation, they have poor photooxidative stability, their availability is uncertain, and it is costly to extract and process them. Thus, their use has been limited. For a number of years, efforts have been underway around the world to produce synthetic cyclopropanecarboxylate insecticides, pyrethroids, which would overcome these disadvantages. 5-Benzyl-3-furylmethyl chrysanthemate (resmethrin) [Elliott, et al., *Nature*, 213, 493 (1967)], a powerful contact insecticide, was an early success. A notable recent result of these efforts was the discovery of the pyrethroid, 3-phenoxybenzyl 3-($\beta,\beta$-dichlorovinyl)-2,2-dimethylcyclopropanecarboxylate, having the combination of toxicity and knockdown attributes of the natural pyrethrins and resmethrin together with a previously unattained level of photooxidative stability [Elliott, et al., *Nature*, 246, 169 (1973); S. African Patent 73/3528].

Although the activity of 3-phenoxybenzyl 3-($\beta,\beta$-dichlorovinyl)-2,2-dimethylcyclopropanecarboxylate as an insect killer is disclosed in the prior art last cited, there has been no suggestion that this pyrethroid would exhibit the variant of insect control which is the subject of this invention - repellency.

SUMMARY OF THE INVENTION

Thus, the instant invention has as its object and provides a method of repelling insect pests, including acarids, which comprises applying to the locus from which such insect pests are to be repelled a repellent amount of 3-phenoxybenzyl 3-($\beta,\beta$-dichlorovinyl-2,2-dimethylcyclopropanecarboxylate; such application may be effected with novel repellent compositions of this invention consisting essentially of no more than about 0.2% by weight 3-phenoxybenzyl 3-($\beta,\beta$-dichlorovinyl)-2,2-dimethylcyclopropanecarboxylate, but any source, manner, or means may be utilized to apply to the locus to be protected a repellent amount of 3-phenoxybenzyl 3-($\beta,\beta$-dichlorovinyl)-2,2-dimethylcyclopropanecarboxylate.

3-Phenoxybenzyl 3-($\beta,\beta$-dichlorovinyl)-2,2-dimethylcyclopropanecarboxylate is capable of controlling, by repelling, a number of different types of insect pests, including acarids; for example, cockroaches, true bugs, flies, mites, aphids, and beetles, as well as mature and immature moths and butterflies. Unusually long residual activity is a characteristic of repelling insect pests with 3-phenoxybenzyl 3-($\beta,\beta$-dichlorovinyl)-2,2-dimethylcyclopropanecarboxylate.

In order that the novel repellent compositions of this invention primarily repel, rather than kill insect pests, when applied to the locus to be protected by means well known in the art, the concentration of 3-phenoxybenzyl 3-($\beta,\beta$-dichlorovinyl)-2,2-dimethylcyclopropanecarboxylate is lower than that typically present in the insecticides of the prior art; that is, the novel repellent compositions of this invention contain no more than about 0.2% by weight 3-phenoxybenzyl 3-($\beta,\beta$-dichlorovinyl)-2,2-dimethylcyclopropanecarboxylate and no other cyclopropanecarboxylate or synergist therefor.

The active component, 3-phenoxybenzyl 3-($\beta,\beta$-dichlorovinyl)-2,2-dimethylcyclopropanecarboxylate, may be prepared from t-butyl chrysanthemate by the method of Elliott, et al. [*Nature*, 244, 456 (1973)].

DESCRIPTION OF THE PREFERRED EMBODIMENTS

The repellent compositions of this invention may take various forms, including solutions, dusts, granular formulations, and emulsions. They may be prepared from concentrates, such as emulsifiable concentrates and wettable powders. Although the compositions of this invention consist essentially of no more than 0.2% by weight 3-phenoxybenzyl 3-(β,β-dichlorovinyl)-2,2-dimethylcyclopropanecarboxylate, various inert ingredients may also be present, depending upon the form taken by the composition.

If prepared from an emulsifiable concentrate, the composition may contain a surfactant such as, for example, a mixture of a polyethylene oxide with a blend of oil soluble non-ionic and anionic sulfonates. The surfactant normally comprises between about 1 and 15% by weight of the emulsifiable concentrate.

Wettable powders can also be used to make the repellent compositions. Compositions so made may be applied to the area to be protected as emulsions in water or other liquid diluents. Typical among the carriers employed in wettable powders are walnut flour, cane sugar, fuller's earth, attapulgite clays, kaolin clays, silicas and other highly absorbent, readily wetted carriers. The wettable powders themselves generally are prepared to contain about 5 to 80% by weight of the active component, depending on the absorbency of the carrier. A wettble powder usually also contains a small amount of a surfactant.

As previously indicated, when an emulsifiable concentrate or wettable powder is diluted to produce a composition of this invention, no more than about 0.2% by weight 3-phenoxybenzyl 3-(β,β-dichlorovinyl)-2,2-dimethylcyclopropanecarboxylate will be present.

Granular repellent compositions, wherein the active component is carried on relatively coarse particles as the carrier, are also useful in repelling crawling insect pests. Dry dusts, in which the active component is admixed with finely divided solids such as talc, attapulgite clay, kieselguhr, and other organic and inorganic solids, which act as carriers for the active component, also find utility. These finely divided solids usually have an average particle size of less than about 50 microns.

Pressurized sprays such as aerosols, in which the active component is present in solution or in a finely divided form, may also be used.

The concentration of 3-phenoxybenzyl 3-(β,β-dichlorovinyl)-2,2-dimethylcyclopropanecarboxylate in any of the repellent compositions of this invention may vary in the range from about 0.00001% to about 0.2% by weight, depending on the formulation. A very broad latitude in the type of repellent composition and the concentration of the active component within the aforesaid range is possible.

In repelling insect pests according to the method of this invention it is only necessary to apply to the locus from which such insect pests are to be repelled a repellent amount of 3-phenoxybenzyl 3-(β,β-dichlorovinyl)-2,2-dimethylcyclopropanecarboxylate, the application being effected in any convenient way. A repellent amount of 3-phenoxybenzyl 3-(β,β-dichlorovinyl)-2,2-dimethylcyclopropanecarboxylate will vary somewhat, depending on the species of insect to be repelled, the nature of the locus, including the type of surface, from which the insects are to be repelled, and so forth, but generally between about 1 mg/m$^2$ and 200 mg/m$^2$ is a repellent amount. As is well known in the art, the degree of effectiveness of the repellent may vary with the formulation and the method of application.

In carrying out the method of this invention, 3-phenoxybenzyl-3-(β,β-dichlorovinyl)-2,2-dimethylcyclopropanecarboxylate may be applied in any suitable fashion to the area in which the repellency of insect pests, including acarids, is desired. Means of effective applications are well known in the art. The repellent activity of 3-phenoxybenzyl 3-(β,β-dichlorovinyl)-2,2-dimethylcyclopropanecarboxylate is illustrated by the following Examples:

EXAMPLE I

The efficacy of 3-phenoxybenzyl 3-(β,β-dichlorovinyl)-2,2-dimethylcyclopropanecarboxylate as a repellent toward the German cockroach (*Blattella germanica* [Linnaeus]) was evaluated in comparison with some other commonly used repellents and insecticides by a "free choice" test method as follows: Filter paper discs (7 cm in diameter) were treated with either pure acetone or a 0.1% solution of one of the following compounds dissolved in acetone: 3-phenoxybenzyl 3-(β,β-dichlorovinyl)-2,2-dimethylcyclopropanecarboxylate, 2-hydroxyethyl octyl sulfide, chlorpyrifos (O,O-diethyl 0-3,4,6-trichloro-2-pyridylphosphorothioate), resmethrin, or deodorized kerosene (a typical component of repellents). The solutions were applied to the discs so as to deposit either about 50 or about 100 mg of the compound per square meter. The discs were dried overnight. Each treated disc was then placed at the bottom of a 20 cm crystalizing dish in which shelter and water were provided.

Cereal pellets (about 2 cm×1.3 cm×1 cm) were weighed and then placed in the center of each treated disc. Fifty adult male cockroaches were then confined in each dish. The cockroaches were allowed to feed on the cereal pellets, which required that they cross the surface of the treated discs. The cereal pellets were reweighed at the end of 24, 48 and 72 hours. The cumulative weight loss for each cereal pellet was recorded, and "percent repellency" was calculated by comparing the weight loss from a cereal pellet resting on a disc treated with one of the aforesaid solutions to the weight loss from a cereal pellet resting on a disc treated with pure acetone. The averaged results for experiments in triplicate appear in Table I.

3-Phenoxybenzyl 3-(β,β-dichlorovinyl)-2,2-dimethylcyclopropanecarboxylate was more efficacious and longer lasting than any of the other compounds, including resmethrin.

Table I

| | | Cockroach Repellency | | | | | |
|---|---|---|---|---|---|---|---|
| | Dose | Difference in Food Consumed (mg)[a] | | | Percent Repellency[a] | | |
| Treatment | (mg/m$^2$) | 24 hr | 48 hr | 72 hr | 24 hr | 48 hr | 72 hr |
| Pyrethroid[b] | 50 | 220 | 163 | 0 | 80 | 37 | 0 |
| | 100 | 263 | 154 | 125 | 56 | 33 | 65 |
| Chlorpyrifos | 50 | 0 | 23 | 38 | 0 | 6 | 11 |

Table I-continued

| Treatment | Dose (mg/m²) | Cockroach Repellency Difference in Food Consumed (mg)[a] | | | Percent Repellency[a] | | |
|---|---|---|---|---|---|---|---|
| | | 24 hr | 48 hr | 72 hr | 24 hr | 48 hr | 72 hr |
| | 100 | 29 | 138 | 0 | 6 | 32 | 0 |
| 2-Hydroxyethyl | 50 | 0 | 0 | 0 | 0 | 0 | 0 |
| octyl sulfide | 100 | 79 | 75 | 0 | 14 | 17 | 0 |
| Resmethrin | 50 | 308 | 0 | 0 | 52 | 0 | 0 |
| | 100 | 0 | 0 | 0 | 0 | 0 | 0 |
| Deodorized | 50 | 0 | 0 | 0 | 0 | 0 | 0 |
| kerosene | 100 | 125 | 62 | 81 | 18 | 14 | 21 |

[a] Weight loss from cereal pellet in dish containing disc treated with acetone (A), less weight loss from cereal pellet in dish containing disc treated with solution (B). Percent Repellency = 100 (A—B)/A
[b] 3-Phenoxybenzyl 3-(β,β-dichlorovinyl)-2,2-dimethylcyclopropanecarboxylate.

EXAMPLE II

The repellent character of 3-phenoxybenzyl 3-(β,β-dichlorovinyl)-2,2-dimethylcyclopropanecarboxylate was also observed in the case of confined foliage-feeding insect pests such as the Mexican bean beetle (*Epilachna varivestis* Mulsant), southern armyworm (*Spodoptera eridania* [Cramer]), pea aphid (*Acrylthosiphon pisum* [Harris]), and the twospotted spider mite, (*Tetranychus urticae* Koch). In these cases, repellency was manifested by the tendency of the pests to migrate from plants which had been treated with 3-phenoxybenzyl 3-(β,β-dichlorovinyl)-2,2-dimethylcyclopropanecarboxylate and escape the holding cages during testing. In order to quantify this tendency, plants upon which the aforesaid pests feed were treated by either dipping them in or spraying them with solutions containing various concentrations of 3-phenoxybenzyl 3-(β,β-dichlorovinyl)-2,2-dimethylcyclopropanecarboxylate in the range of 0 to 1250 ppm on a wt/wt basis. The plants were then infested with a counted number (at least 20 individuals) from one of the insect pest species, either immediately, or after seven days (to test the residual effect of the treatment). A cage was secured around the foliage of each infested plant; such cages normally confine the pests, although escape is possible, for example, at the point where the stem of the plant enters the cage. The number of individual pests remaining on an infested plant was determined 48 hours after infestation, and the fraction of the pests repelled from the plant was taken to be the difference between the original and final counts divided by the original count. The results appear in Table 2.

Table 2

| Solution concentration (ppm)[b] | Foliage-Feeder[a] Repellency Percent Repelled | | | | | | | |
|---|---|---|---|---|---|---|---|---|
| | Initial | | | | 7-Day Residual | | | |
| | SM | PA | AW | BB | SM | PA | AW | BB |
| 1250 | 39 | | | | 41 | | | |
| 625 | 65 | | | | 17 | | | |
| 156 | 47 | | | | 55 | | | |
| 39 | 30 | 0 | 0 | 0 | 60 | 0 | | 60 |
| 10 | | 50 | | | 20 | | | |
| 2.5 | | 70 | | | | | | |
| 1.2 | | | 20 | 20 | | | 35 | 50 |
| 0.3 | | | 30 | 30 | | | 5 | 0 |
| 0.075 | | | 0 | 0 | | | | |
| 0.0 | 4.2 | 0 | 0 | 0 | 0 | 0 | 0 | 0 |

[a] SM = twospotted spider mite
PA = pea aphid
AW = southern armyworm
BB = Mexican bean beetle
[b] 3-Phenoxybenzyl 3-(β,β-dichlorovinyl)-2,2-dimethylcyclopropanecarboxylate.

EXAMPLE III

The repellency of 3-phenoxybenzyl 3-(β,β-dichlorovinyl)-2,2-dimethylcyclopropanecarboxylate toward the tobacco hornworm (*Manduca sexta* [Linnaeus]) was evaluated as follows:

An emulsifiable concentrate was diluted with water and sprayed at a level of about 55 pyrethroid per hectare onto growing tobacco plants having 14 to 16 leaves exposed. Periodically thereafter, counts were made of the number of tobacco hornworm larva present per 30 plants. Similar counts were made on untreated tobacco plants. The results were as follows:

| Time After Treatment | Larva per 30 Plants | |
|---|---|---|
| | Treated | Untreated |
| 3 days | 1.63 | 131 |
| 6 days | 0.27 | 165 |
| 10 days | 1.16 | 233 |

That the pyrethroid was effective as a repellent rather than as a killer was evidenced by the complete absence of foliar damage to the treated plants.

We claim:

1. A method of repelling a species of insect from a locus to which said species of insect is normally attracted which comprises depositing on said locus a non-toxic effective insect repellent amount of a formulation consisting essentially of no more than about 0.2% by weight 3-phenoxybenzyl 3-(β,β-dichlorovinyl)-2,2-dimethylcyclopropanecarboxylate and no other cyclopropanecarboxylate or synergist therefor in intimate admixture with a carrier or diluent therefor.

2. A method according to claim 1, wherein the formulation contains about 0.3 to 1250 parts per million of 3-phenoxybenzyl 3-(β,β-dichlorovinyl)-2,2-dimethylcyclopropanecarboxylate.

3. A method according to claim 1, wherein the formulation is a solution, dust, granular formulation or emulsion.

4. A method according to claim 3, wherein the formulation contains about 0.3 to 1250 parts per million of 3-phenoxybenzyl 3-(β,β-dichlorovinyl)-2,2-dimethylcyclopropanecarboxylate.

5. A method according to claim 1, wherein the formulation is a liquid solution or emulsion.

6. A method according to claim 5, wherein the formulation contains about 0.3 to 1250 parts per million of 3-phenoxybenzyl 3-(β,β-dichlorovinyl)-2,2-dimethylcyclopropanecarboxylate.

* * * * *